(12) United States Patent
Metzger

(10) Patent No.: US 6,344,176 B1
(45) Date of Patent: Feb. 5, 2002

(54) DEVICE FOR TREATING LIQUIDS, ESPECIALLY COOLANTS AND LUBRICANTS

(76) Inventor: Juergen Metzger, Wagenstrasse 1a, 78532 Tuttlingen (DE)

( * ) Notice: Subject to any disclaimer, the term of this patent is extended or adjusted under 35 U.S.C. 154(b) by 0 days.

(21) Appl. No.: 09/452,953

(22) Filed: Dec. 2, 1999

(30) Foreign Application Priority Data

Dec. 2, 1998 (DE) .................................... 298 21 502 U

(51) Int. Cl.$^7$ .............................................. B01J 19/08
(52) U.S. Cl. ..................................... 422/186.3; 422/24
(58) Field of Search ................................ 422/186.3, 24

(56) References Cited

U.S. PATENT DOCUMENTS 3,926,556 A * 12/1975 Boucher ...................... 422/24
5,997,812 A * 12/1999 Burham et al. ................ 422/24

* cited by examiner

Primary Examiner—Kishor Mayekar
(74) Attorney, Agent, or Firm—Crowell & Moring LLP

(57) ABSTRACT

A device for treating liquids, especially coolants and lubricants for machining materials involving chip removal, is provided, and combats the problems of biological decomposition, biological collapse, and attacks by viruses and microorganisms such as fungi and bacteria. The device includes a device for producing a liquid film and a UV radiation unit for zero-contact irradiation of the film.

11 Claims, 2 Drawing Sheets

DEVICE FOR TREATING LIQUIDS, ESPECIALLY COOLANTS AND LUBRICANTS

BACKGROUND AND SUMMARY OF THE INVENTION

This application claims the priority of German Application No. 298 21 502.0, filed Dec. 2, 1998, the disclosure of which is expressly incorporated by reference herein.

The invention relates to a device for treating liquids, especially coolants and lubricants.

Coolants and lubricants (hereinafter called CLs) are being used increasingly in machining of metals, glass, ceramics, and so forth involving chip removal. A CL is used in particular for cooling the tool and workpiece, for lubrication and hence reducing the heat of friction as well as the cutting forces and for cleaning the workpiece or tool to be machined by flushing away chips and impurities. Water-miscible CLs, which are either emulsified or dissolved in water, are usually used. CLs have lubrication as their primary function while the water is primarily responsible for cooling. In accordance with the present invention, the terms CL and CL emulsion are used interchangeably.

When CLs are used, they become increasingly loaded with foreign matter. Such foreign matter consists in particular of foreign oils, as well as contamination which results in particular from machining involving chip removal. Also, the CLs themselves can be broken down by decomposition processes. Finally, the CLs can be attacked by viruses or microorganisms such as bacteria, yeasts, and/or fungi which can lead to biological decomposition making them unsuitable as CLs. A highly unpleasant formation of odors is normally associated with biological decomposition. Microorganisms can even cause biological collapse of CL baths. Attacks by fungi can lead to clogging of the CL line which results in tedious and costly maintenance and repair work and hence in expensive downtimes.

To increase the service life of CLs, measures are known in conventional devices which serve to eliminate these foreign substances. Contamination by foreign substances is removed by separators and/or filters. It is also known to blow fine air bubbles into the CL. The fine air bubbles attach themselves to the foreign substances, significantly increasing their buoyancy, and the CLs are consequently separated more rapidly from foreign substances. However, when air is added, undesired enrichment with aerobic bacteria can occur which intensifies the problem of biological decomposition and biological collapse of CL baths.

In other applications as well, for example washing systems, drinking water circuits, and so forth, the problem of biological decomposition or contamination frequently occurs as well as biological collapse and attacks by viruses as well as microorganisms such as fungi and bacteria.

The goal of the invention is to provide a device for treating liquids, especially coolants and lubricants, that combats the problems of biological decomposition, biological collapse, and attacks on the CLs by viruses as well as microorganisms such as fungi and bacteria for example.

This goal is achieved by a device for treating liquids, especially coolants and lubricants (CLs) for use in machining materials involving chip removal, wherein a device for creating a liquid film and a UV radiation unit for zero-contact irradiation of the liquid film are provided.

By the measures described herein, advantageous embodiments and improvements on the invention are possible.

Accordingly, a device according to the invention is characterized by the fact that a device is provided for producing a liquid film and a UV radiation unit for zero-contact irradiation of the film.

The thin form of the film makes it possible for the UV radiation to completely penetrate the film and thus subject it completely to the disinfectant action of the UV radiation. As a result of the zero-contact irradiation of the liquid, the surface of the UV radiation unit remains free of any deposits that normally occur when the UV radiator is submerged in the liquid, for example in the CL, rendering the surface of the UV radiator non-transparent to the desired UV radiation so that it must be replaced or subjected to expensive cleaning. As a result of the zero-contact irradiation of the liquid film, the service life of the UV radiation unit is much longer.

In one especially advantageous embodiment of the invention, the liquid film is applied to a film carrier. A film carrier of this type can be provided for example in the form of a diagonal plate on which the liquid, such as CL or water, can flow downward in a thin film.

Such a flat flow section can however, in the case of impurities or projections, cause the liquid film to separate. Although the effect of the UV radiation does not depend on the formation of a continuous flat film, the efficiency of the device according to the invention is increased by having an area that is irradiated to the greatest degree possible while the film thickness remains sufficiently thin.

Therefore, in one advantageous improvement on a film carrier, the film carrier is made movable. As a result, the flow rate of the liquid film on the film carrier is reduced. With suitable adjustment of the movement of the film carrier, relative movement between the film carrier and the liquid film can be largely suppressed. In this case, there is a stable flat film in the vicinity of the UV radiation unit which can be in defined in terms of its film thickness.

A movable film carrier can be obtained in different ways, for example in the form of a circulating carrier belt, rotating disks, etc. In one preferred embodiment, a rotating drum is provided as the film carrier, whose jacket surface serves as the carrying surface of the film. Such a carrier drum is comparatively inexpensive to manufacture and to drive. In addition, the jacket surface of the carrier drum that serves as the carrier surface can be irradiated easily from outside by means of a UV radiation unit.

In one advantageous embodiment of the invention, the liquid film is applied in the area of the UV radiation in a downward movement on the film carrier so that the movement of the carrier coincides with the natural flow direction of the liquid. As a result, as outlined above, the relative movement between the liquid film and the film carrier can be considerably reduced.

In the case of a more viscous liquid, however, it is readily possible to apply a liquid film to a film carrier in an upward movement as well.

In one especially advantageous embodiment of the invention, the film carrier receives the flow of liquid. In this case, for example, a pouring head can be used in which the liquid can flow out of a reservoir through an outlet opening or nozzle onto the carrier surface of the film carrier. In the case of a movable film carrier, the liquid is transported by the film carrier as soon as it strikes the carrying surface of the film carrier. In the case of a static film carrier, as mentioned above, the liquid flows downward onto the carrier surface in the direction of a UV radiation unit.

A pouring head of this type could also have an overflow for film formation instead of an opening or nozzle.

To produce a liquid film, it would also be possible in another embodiment to spray the liquid onto the carrier surface of the film carrier. This is possible for example with the aid of a suitable nozzle arrangement by which the liquid is atomized at an appropriate pressure. The atomized liquid can then precipitate onto the carrier surface of the film carrier and form the desired flat film there.

In another possible embodiment of the invention, the film carrier with its carrier surface is introduced into a dip bath of the liquid. By an appropriate upward movement of the carrier surface, when the liquid has suitable adhesion and viscosity, a film can be applied to the film carrier. A film carrier of this kind could be for example a drum rotatably mounted and located partially in the dip bath or one or more rotatable disks partially located in the dip bath.

In one advantageous embodiment of the invention, the carrier surface is provided with a surface structure by which the adhesion of the liquid or film formation is improved. This surface structure can be formed by a suitable roughness or relief structure. However it is also possible to improve film formation by coating with a suitable material.

In addition, the surface of the film carrier can be so designed that its surface reflects the applied UV radiation. As a result, the efficiency of the device according to the invention can be significantly increased. The film thickness can be made so small that the UV radiation strikes the carrier side as well with an intensity that is still highly effective, is reflected at the carrier surface, and thus passes through the film again in the opposite direction. As a result, a more homogeneous irradiation of the film, and hence more efficient disinfection of the liquid, are possible.

In order to separate the liquid from the film carrier, a wiper is preferably provided. Especially in the case of a movable film carrier, assurance is reliably provided that the liquid will be removed completely and no residue will remain on the carrier surface that would reduce the amount of new liquid accepted during a new application.

The carrier surface is freed of any impurities by the wiper as well. This function is advantageous especially in static film carriers, for example a diagonal flow section. In this case, the wiper can be made movable, for example like a windshield wiper. In the case of a movable film carrier, the wiper can be mounted for example as a static wiping lip since the relative movement between the wiper and the film carrier is produced by the movement of the film carrier.

In addition, a wiper provides a specific location for removal of the disinfecting liquid from the film carrier so that a suitable collecting container or funnel can be made smaller than would be the case for example if the liquid were to drip freely.

In another embodiment of the invention, instead of the liquid film carried on the film carrier, a free-falling liquid film is irradiated. A device with a free-falling liquid film is described for example in German Utility Model 29 821 502, which establishes priority. Reference is expressly made here to the entire disclosure content of this document.

A free-falling liquid film can be produced for example by a nozzle which is made flat or as a double ring nozzle for example. In the case of an outlet opening from the nozzle that is vertical or near-vertical, the film can be produced exclusively by the weight of the liquid in a reservoir located above. In an improvement on this embodiment, a pressure pump is also provided that delivers the liquid under pressure through the corresponding nozzle in order to form the corresponding film. In this case, spray devices are also possible which branch off from the vertical falling direction, for example in horizontal outflow directions or even with ejection at an angle.

Advantageously, the UV radiation unit, as described previously in the document establishing priority, is provided with an optical element to influence the radiation characteristic, for example a parabolic mirror which reflects the radiation coming from the UV radiator toward the liquid film and onto the liquid film. The parabolic mirror design produces a nearly parallel beam path of the reflected radiation. By means of such optical elements, the efficiency of the device according to the invention can be increased further so that, as a result, fewer or less expensive UV radiators can be used.

In an improvement on the invention, a plurality of UV radiators are provided which can include all optical elements for influencing the radiation characteristics. As a result, a flatter radiation can be produced. The size of the irradiated surface can then be adjusted to the film thickness, delivery rate of the film in front of the UV radiator, and the corresponding attacks by microorganisms in such a way that sufficient desired disinfection takes place.

Advantageously the quantity of liquid that passes in front of the UV irradiation unit is regulated. This is possible for example by controlling the film thickness. The film thickness in turn can be adjusted for example by corresponding cross sections of the outflow openings or nozzles and/or by the pressure of the liquid that causes the flow.

The pressure of the liquid in turn can be varied for example by regulating the delivery pressure of a delivery pump. Metering valves, for example in the form of regulating throttles or timed valves, can be used for this purpose.

For a flow that is as uniform as possible over the entire film width, however, it has proven successful to provide a reservoir above the outflow opening or nozzle. In this case, the volume of the liquid can be regulated by controlling the fullness of the reservoir. For example electronic controls can be used that measure the fullness, in conjunction with a suitable metering valve. Other designs provide a height-adjustable overflow. In order to make the quantity flowing over such an overflow independent of the volume flowing through the line, the overflow can take place in a bypass line to feed the liquid to the reservoir, which branches off from the supply to the reservoir and terminates in the reservoir usually provided in such chip-removing machines. Another possibility for regulating the level in a reservoir is to use a float valve.

Other objects, advantages and novel features of the present invention will become apparent from the following detailed description of the invention when considered in conjunction with the accompanying drawings.

DETAILED DESCRIPTION OF THE DRAWINGS

Figure 1:
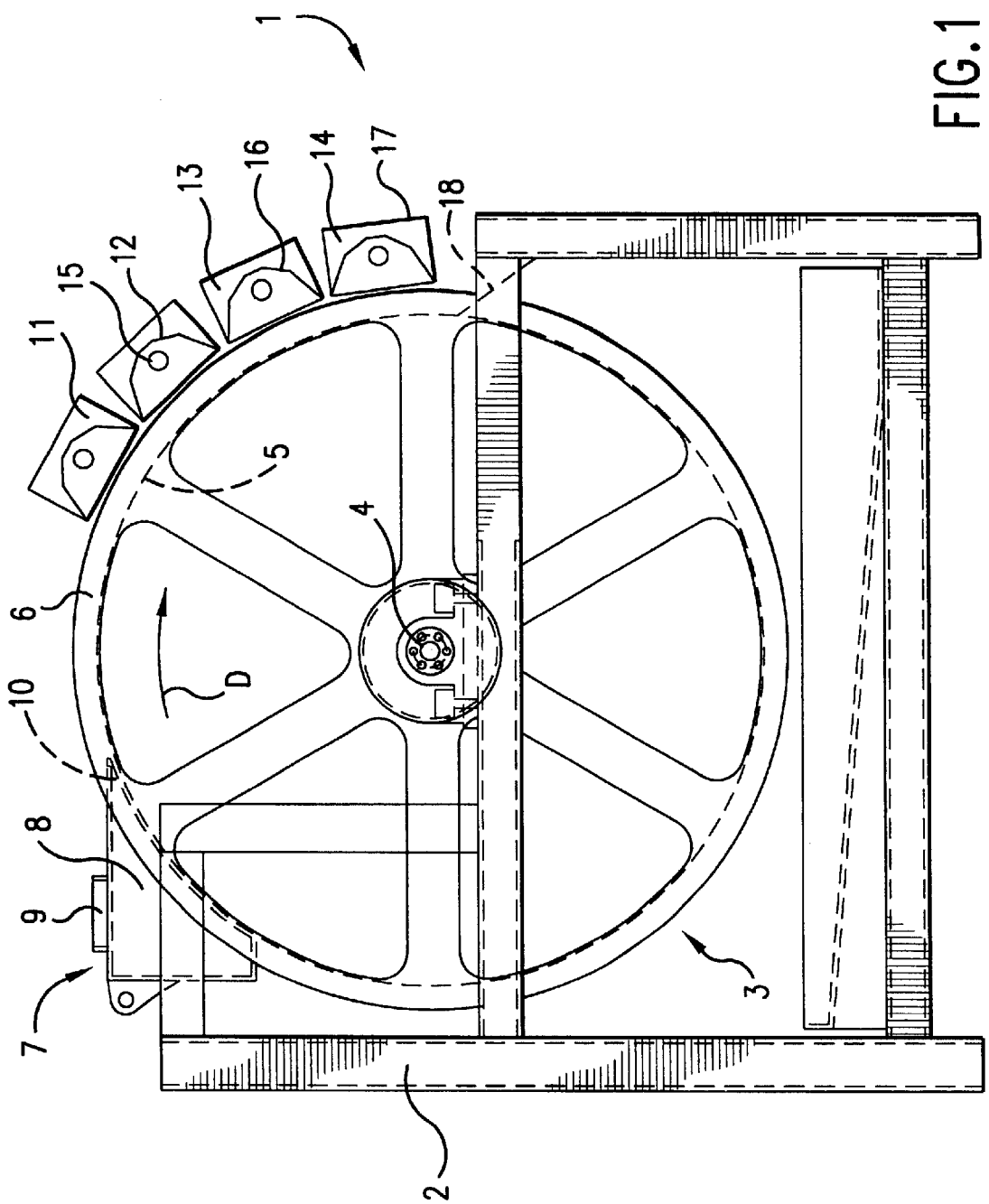
FIG. 1 is a schematic side view of a device according to the invention.
Figure 2:
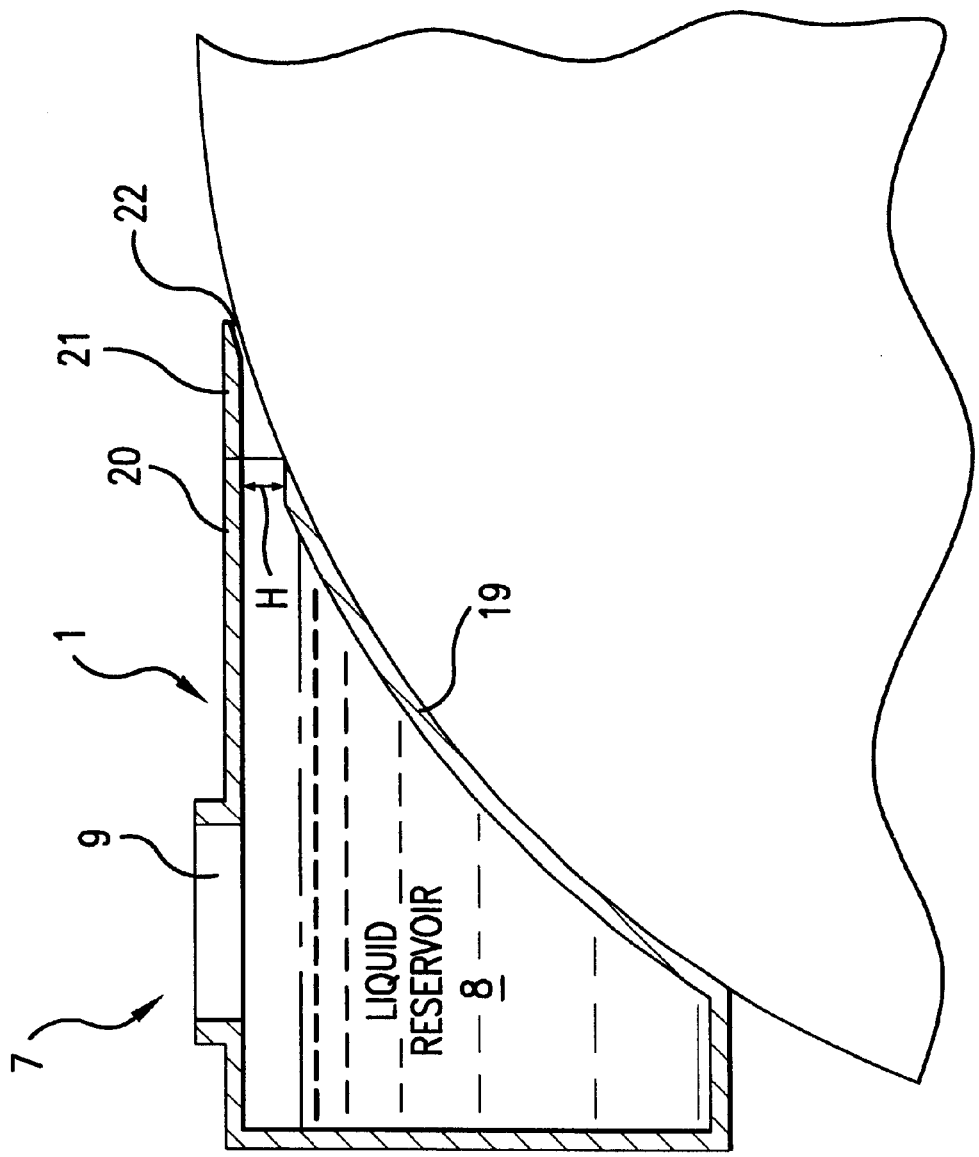
FIG. 2 shows an enlargement of a portion of a pouring head of a device according to the invention and according to FIG. 1.

Device 1 according to FIG. 1 comprises a frame 2 on which a carrier drum 3 is mounted to rotate around an axis 4. Carrier drum 3 comprises a carrier surface 5 designed as a cylindrical jacket surface and delimited endwise by edge flange 6. A pouring head 7, consisting of a reservoir 8 (see FIG. 2 in particular), a filling opening 9, and an outlet opening 10 is located in the upper part of carrier drum 3. In rotational direction D, four UV irradiation units 11, 12, 13, and 14 are arranged along carrier surface 5.

Each UV radiation unit 11, 12, 13 and 14 comprises a UV radiator 15 located at the focus of a parabolic mirror 16 in a housing 17.

Located downstream in rotational direction D of UV radiation units 11, 12, 13, and 14 is a wiper 18 which wipes the liquid film, for example the CL film or water film, off carrier surface 5. The liquid, for example the CL, is then collected in a collecting tank not shown in greater detail and returned to the liquid circuit.

The level in reservoir 8 moves during operation within the range H that corresponds to the level of outlet opening 10. Reservoir 8 is adapted on its underside 19 to the contour of carrier surface 5. Particularly in the area of outlet opening 10, container wall 19 is adjacent carrier surface 5 so that the CL, water, and so forth flowing through outlet opening 10 are applied directly to carrier surface 5. The upper container wall 20 continues in an extension 21 parallel to carrier surface 5 thus forming a gap 22 through which the liquid film is delivered.

The rotational speed of carrier drum 3, like the level in range H, constitutes a control parameter for regulating the volume of the transported liquid, for example CL. The higher the level in section H, the thicker the liquid film delivered through gap 22 and adhering to carrier surface 5. The faster carrier drum 3 rotates, the greater the amount delivered per unit time from reservoir 8.

As carrier drum 3 turns, the liquid film on carrier surface 5 is transported beneath UV radiation units 11, 12, 13, and 14. The liquid, for example the CL, is penetrated by the UV light from UV radiation units 11, 12, 13 and 14 and disinfected accordingly.

By placing UV radiator 15 at the focus of parabolic mirror 16, the entire UV radiation is focused on the liquid film.

Carrier surface 5 can be designed as a UV mirror in a preferred embodiment. In this case, it is recommended to make the ratio between the UV radiation intensity and the film thickness such that the UV radiation strikes carrier surface 5 designed as a reflecting surface with sufficient intensity and is reflected back from there into the liquid film. In this way, a more homogeneous irradiation of the liquid film with UV light and hence more homogeneous disinfection are achieved.

Device 1 shown here constitutes only one special embodiment of the invention. It is important in this regard that the liquid, for example the CL, is formed as a thin film which can be irradiated by UV radiators 15 with zero contact.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

TABLE OF REFERENCE NUMERALS 1 device
2 frame
3 carrier drum
4 rotational axis
5 carrier surface
6 edge flange
7 pouring head
8 reservoir
9 filling opening
10 outflow opening
11 UV radiation units
12 UV radiation units
13 UV radiation units
14 UV radiation units
15 UV radiator
16 parabolic mirror
17 housing
18 wiper
19 container wall
20 container wall
21 extension
22 gap

What is claimed is:

1. Device for treating liquids, comprising:
    a carrier drum having an outer surface, said carrier drum being rotatable around a horizontal axis;
    a pouring head having an outlet opening located adjacent to an upper portion of the outer surface of the carrier drum, said pouring head configured to dispense a film of the liquid onto the outer surface of the carrier drum;
    a wiper arranged at an angular distance from the pouring head about the outer surface of the carrier drum to remove the liquid film from the outer surface of the carrier drum; and
    a plurality of UV radiation units arranged exteriorly to the outer surface of the carrier drum between the pouring head and the wiper to directly irradiate the liquid film on the outer surface of the carrier drum without contacting the liquid film.

2. Device according to claim 1, wherein the pouring head sprays the liquid film on the outer surface of the carrier drum.

3. Device according to claim 1, wherein a volume of liquid transported is regulated by regulating a rotational speed of the rotatable carrier drum.

4. Device according to claim 1, wherein a volume of the liquid transported is regulated by a fullness regulating device in the pouring head.

5. Device according to claim 1, wherein the carrier drum is located in a dip bath.

6. Device according to claim 1, wherein the carrier drum has a surface structure in the outer surface.

7. Device according to claim 6, wherein the outer surface of the carrier drum is designed as a UV mirror.

8. Device according to claim 1, wherein a nozzle is provided to create the liquid film.

9. Device according to claim 1, wherein at least one of the UV radiation units is provided with an optical element to increase the UV radiation striking the liquid film.

10. The device according to claim 1, wherein the liquid is a coolant and lubricant for machine tools.

11. A machine for machining workpieces in which chips are removed from the workpieces, comprising:
    a cooling and lubricant circuit adapted to contain coolants and lubricants used in the machining of the workpieces to at least collect the chips removed from the workpieces; and
    a device for treating the coolants and lubricants in said circuit, the device comprising:
        a carrier drum having an outer surface, said carrier drum being rotatable around a horizontal axis;
        a pouring head having an outlet opening located adjacent to an upper portion of the outer surface of the carrier drum, said pouring head configured to dispense a film of the liquid onto the outer surface of the carrier drum;

a wiper arranged at an angular distance from the pouring head about the outer surface of the carrier drum to remove the liquid film from the outer surface of the carrier drum; and a plurality of UV radiation units arranged exteriorly to the outer surface of the carrier drum between the pouring head and the wiper to directly irradiate the liquid film on the outer surface of the carrier drum without contacting the liquid film.

* * * * *